(12) United States Patent
Son et al.

(10) Patent No.: US 12,002,148 B2
(45) Date of Patent: Jun. 4, 2024

(54) METHOD AND APPARATUS FOR THREE-DIMENSIONALLY VISUALIZING ROOT CANAL CURVATURE OF TOOTH

(71) Applicants: Ewoosoft Co., Ltd., Gyeonggi-do (KR); VATECH EWOO Holdings Co., Ltd., Gyeonggi-do (KR)

(72) Inventors: Tae Min Son, Gyeonggi-do (KR); Min Kyung Cuhn, Gyeonggi-do (KR); Mi Yong Kim, Gyeonggi-do (KR)

(73) Assignees: Ewoosoft Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 613 days.

(21) Appl. No.: 17/135,198

(22) Filed: Dec. 28, 2020

(65) Prior Publication Data
US 2021/0196214 A1 Jul. 1, 2021

(30) Foreign Application Priority Data
Dec. 27, 2019 (KR) .................... 10-2019-0176315

(51) Int. Cl.
*G06T 15/20* (2011.01)
*G06T 15/08* (2011.01)
*G06T 19/20* (2011.01)

(52) U.S. Cl.
CPC ............ *G06T 15/205* (2013.01); *G06T 15/08* (2013.01); *G06T 19/20* (2013.01); *G06T 2215/06* (2013.01)

(58) Field of Classification Search
None
See application file for complete search history.

(56) References Cited

U.S. PATENT DOCUMENTS

| | | |
|---|---|---|
| 6,842,638 B1 | 1/2005 | Suri et al. |
| 2009/0162813 A1 | 6/2009 | Glor et al. |
| 2011/0164064 A1 | 7/2011 | Tanaka et al. |
| 2011/0216951 A1 | 9/2011 | Ye et al. |
| 2012/0041446 A1* | 2/2012 | Wong .................. A61F 2/30756 606/86 R |

(Continued)

FOREIGN PATENT DOCUMENTS

| | | | |
|---|---|---|---|
| CN | 101604354 A | | 12/2009 |
| CN | 105852971 A | * | 8/2016 |

OTHER PUBLICATIONS

Estrela, Carlos, et al. ("Method for determination of root curvature radius using cone-beam computed tomography images." Brazilian Dental Journal 19 (2008): 114-118) (Year: 2008).*

(Continued)

*Primary Examiner* — Nurun Flora
(74) *Attorney, Agent, or Firm* — IP Legal Services, LLC

(57) ABSTRACT

Disclosed are a method of and an apparatus for 3D visualization of the root canal curvature of a tooth. The method includes (a) displaying a CT image of one or more teeth on the basis of CT image data, (b) three-dimensionally rendering at least a portion of the root canal of a target tooth when a dental practitioner selects the target tooth from the CT image, and (c) visualizing a curvature in a region of the root canal that is three-dimensionally rendered using a visual factor.

11 Claims, 9 Drawing Sheets
(7 of 9 Drawing Sheet(s) Filed in Color)

(56) References Cited

U.S. PATENT DOCUMENTS

2012/0239364 A1* 9/2012 Glor .................. A61C 13/0004
                                                           703/11
2015/0099241 A1* 4/2015 Cheng .................. A61C 1/084
                                                           433/196
2019/0125290 A1    5/2019 Arai et al.

OTHER PUBLICATIONS

English translation of Zhang et al. is provided (Year: 2016).*
Balázs Benyó, "Identification of dental root canals and their medial line from micro-CT and cone-beam CT records" BioMedical Engineering OnLine, Oct. 29, 2012, p. 81, vol. 11, No. 1, BioMed Central Ltd., London, GB.
Carlos Estrela et al., "Method for Determination of Root Curvature Radius Using Cone-Beam Computed Tomography Images", Brazilian Dental Journal, Jan. 1, 2008, pp. 114-118.
L. Bergmans et al., "A methodology for quantitative evaluation of root canal instrumentation using microcomputed tomography", International Endodontic Journal, Jul. 1, 2001, pp. 390-398, vol. 34, No. 5, Blackwell Science Ltd.
European Patent Office, European Search Report of corresponding EP Patent Application No. 21150852.8, dated May 19, 2021.
The State Intellectual Property Office of People's Republic of China, Office Action of corresponding CN Patent Application No. 202011558561.5, Jan. 2, 2024.

* cited by examiner

METHOD AND APPARATUS FOR THREE-DIMENSIONALLY VISUALIZING ROOT CANAL CURVATURE OF TOOTH

CROSS REFERENCE TO RELATED APPLICATION

The present application claims priority to Korean Patent Application No. 10-2019-0176315, filed Dec. 27, 2019, the entire contents of which is incorporated herein for all purposes by this reference.

BACKGROUND OF THE INVENTION

1. Field of the Invention

The present invention relates to an image processing technology for dental radiography. More particularly, the present invention relates to a technology for automatically calculating and visualizing the root canal curvature of a tooth on the basis of dental image data obtained through computed tomography (CT).

2. Description of the Related Art

In dentistry, neurotherapy is performed to remove damaged pulp tissue when there are severe caries. For nerve treatment, a tool known as a file is used to remove damaged pulp tissue in the root canal of the tooth. Since this file is typically thin, when the root canal of a tooth to be treated has a large curvature, there is a risk that the file is broken due to severe stress. When the file is broken in the root canal, it is difficult to remove the broken file and the remaining file may cause secondary inflammation.

Therefore, in order to successfully perform neurological treatment on a tooth, care must be taken not to break the file. To this end, the root canal curvature of a tooth should be checked and a severely curved portion of the root canal should be identified in advance. Conventionally, to determine the root canal curvature of a tooth, a region corresponding to the root canal is marked on a two-dimensional X-ray image, the curved portion of the root canal is roughly identified by the naked eyes, a circumscribed circle is drawn around the curved portion of the root canal, and the curvature of the root canal is estimated. However, this method has a problem in that it is difficult to estimate the root canal curvature because when the root canal extends in the Z axis which cannot be identified on a two-dimensional X-ray image. In addition, since a dentist or endodontist has to draw lines and circles to mark the root canal curvature by himself/herself after visually checking the root canal with his/her eyes, it is cumbersome, and errors are likely to occur.

SUMMARY OF THE INVENTION

An objective of the present invention is to provide a method and apparatus for three-dimensionally visualizing the root canal curvature of a tooth on the basis of CT image data of the tooth so that a dental practitioner can easily determine the root canal curvature of a tooth.

The effects, features, and objectives of the present invention are not limited to the ones mentioned above, and other effects, features, and objectives not mentioned above can be clearly understood by those skilled in the art from the following description.

In one aspect, a method of three-dimensionally visualizing the curvature of the root canal of a tooth includes: (a) displaying a CT image of one or more teeth on the basis of CT image data of the one or more teeth; (b) three-dimensionally rendering at least a portion of the root canal of a target tooth when a dental practitioner selects the target tooth on the CT image; and (c) representing a curvature of at least a portion of the root canal that is three-dimensionally rendered in a visually identifiable manner.

According to embodiments of the present invention, there is a technical effect that a dental practitioner can easily check the root canal curvature of a tooth of interest by three-dimensionally visualizing the root canal curvature of the tooth root canal on the basis of CT image data of the tooth.

BRIEF DESCRIPTION OF THE DRAWINGS

The patent or application file contains at least one drawing executed in color. Copies of this patent or patent application publication with color drawings will be provided by the Office upon request and payment of the necessary fee.

DESCRIPTION OF THE PREFERRED EMBODIMENTS

The advantages and features of the present invention and the manner of achieving them will become apparent with reference to the embodiments described in detail below and the accompanying drawings. The present invention may, however, be embodied in many different forms and should not be construed as being limited to the embodiments set forth herein. Rather, these embodiments are provided so that the present invention will be thorough and complete and will fully convey the concept of the invention to those skilled in the art. Thus, the present invention will be defined only by the appended claims.

The terminology used herein is for the purpose of describing particular embodiments only and is not intended to limit the scope of the present invention. For example, a constituent element expressed in the singular form should be understood as a concept including a plurality of constituent elements unless it clearly means only a singular element in the context. It will be further understood that the terms "comprises", "includes", or "has" when used in the present disclosure specify the presence of stated features, regions, integers, steps, operations, elements and/or components, but do not preclude the presence or addition of one or more other features, regions, integers, steps, operations, elements, components and/or combinations thereof. In addition, in the embodiments described herein, a "module" or "unit" may refer to a functional part that performs at least one function or operation.

In addition, unless otherwise defined, all terms including technical and scientific terms used herein have the same meaning as commonly understood by those who are ordinarily skilled in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Hereinafter, preferred embodiments of the present invention will be described in detail with reference to the accompanying drawings. However, in the following description, when there is a concern that the subject matter of the present invention may be unnecessarily obscured, detailed descriptions of well-known functions or configurations will be omitted.

Figure 1:
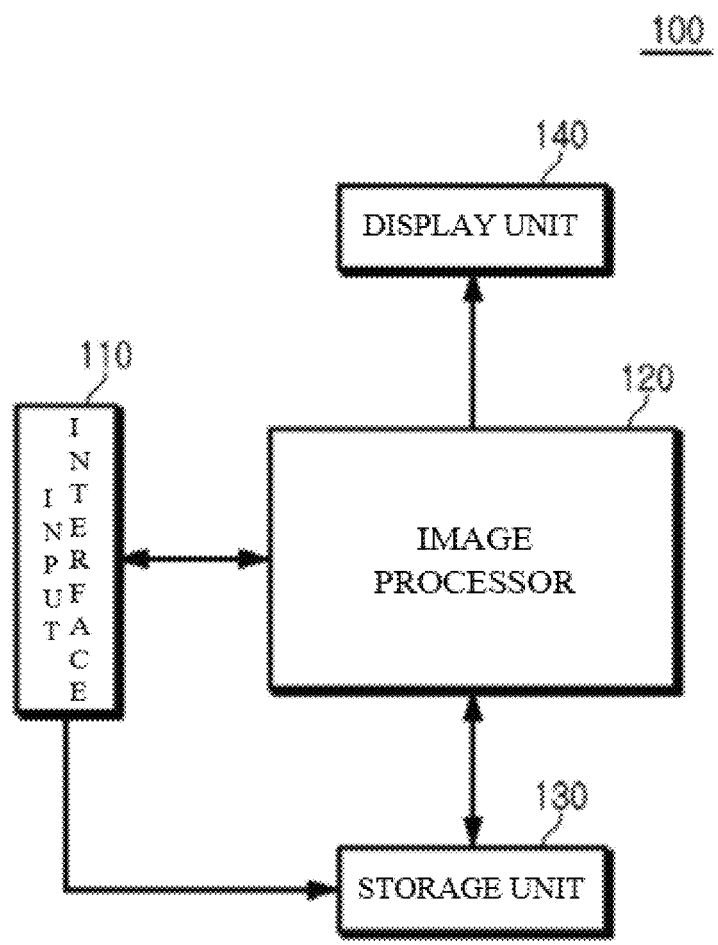
FIG. 1 is a block diagram illustrating an apparatus for three-dimensional visualization of the root canal curvature of a tooth, according to one embodiment of the present invention.

FIG. 1 is a block diagram illustrating an apparatus for three-dimensionally visualizing the root canal curvature of a tooth, according to one embodiment of the present invention.

Referring to FIG. 1, the 3D-visualization apparatus 100 includes an input interface 110, an image processor 120, a storage unit 130, and a display unit 140. The input interface 110 is composed of hardware and software modules that allow a depending on embodiments to input commands or instructions to perform image processing operations in various embodiments of the present invention. The input interface 110 is used to input various commands or instructions to the image processor 120 or to input various types of image data such as CT image data for at least one tooth acquired through CT scans so that the image data can be stored in the storage unit 130 and various image processing operations can be performed on images displayed on the display unit according to the commands or instructions input through the input interface 110. The input interface 110 is advantageously used to specify an arbitrary point in a dental CT image or a dental panoramic X-ray image. In one embodiment, the input interface 110 includes a keyboard, a keypad, a touch-pad, a mouse, etc., but the type of the input interface is not limited thereto. For example, the input interface 110 includes a graphic user interface (GUI) that can be controlled with the input devices. Such a graphical user interface includes a means for implementing a navigator including an upper limit line, a lower limit line, and a reference line on a screen. The display unit 140 displays various images depending on embodiments of the present invention and includes a display device such as an LCD display, an LED display, an AMOLED display, and a CRT display.

The storage unit 130 is used to store data of various images such as CT images of at least one tooth acquired through CT scanning. The storage unit 130 is used to store image data of intermediate results obtained through image processing operations in various embodiments of the present invention, image data of final results obtained through image processing operations in various embodiments of the present invention, and the values of variables required to perform the image processing operations in various embodiments of the present invention. In various embodiments, the storage unit 130 stores the aforementioned various images in the DICOM format or a general image file format such as BMP, JPEC, TIFF, etc. In addition, the storage unit 130 stores software and/or firmware required for implementation of the image processor 120. The storage unit 130 is implemented with a flash memory, a hard disk, a multimedia card (MMC), a card-type memory (for example, secure digital (SD) card, extreme digital (XD) card, etc.), a random accessory memory (RAM), a static random access memory (SRAM), a read-only memory (ROM), an electrically programmable read-only memory (ROM), an electrically erasable programmable read-only memory (EEPROM), a programmable read-only memory (PROM), a magnetic memory, a magnetic disk, or an optical disk. However, those skilled in the art will appreciate that the form of the storage unit 130 is not limited thereto.

The image processor 120 is configured to display a CT image of at least one tooth on the display unit 140 on the basis of dental CT image data. In one embodiment, the image processor 120 is configured to generate a panoramic X-ray image of at least one tooth on the basis of CT image data and display the panoramic X-ray image on the display unit 140. When the dental practitioner selects a target tooth (i.e., tooth of interest) from among at least one tooth within a CT image or a panoramic X-ray image, the image processor 120 three-dimensionally renders at least a portion of the root canal of the target tooth to produce a three-dimensionally rendered image of the root canal. In one embodiment, the selection of a target tooth among at least one tooth within a CT image or a panoramic X-ray image is performed in a manner that the dental practitioner places a navigator on the CT image or the panoramic X-ray image through the input interface 110. In one embodiment, the image processor 120 calculates 3D coordinates of the root canal of the target tooth on the basis of the CT image data by using an algorithm such as an edge detection algorithm, an image segmentation algorithm, and the like, and three-dimensionally renders at least a portion of the root canal of the target tooth on the basis of the calculated 3D coordinates.

In one embodiment, when the dental practitioner selects a target tooth from a CT image or a panoramic X-ray image, the image processor 120 performs an operation of displaying cross-sectional images, each being taken along a direction crossing the longitudinal direction of the target tooth on the basis of the CT image data. In one embodiment, when the dental practitioner sequentially designates multiple positions along the longitudinal direction of the target tooth one after another, the image processor 120 generates and displays cross-sectional images corresponding to the respective positions one after another on the display unit 140. In one embodiment, when the dental practitioner places a navigator on a target tooth on a CT image or a panoramic X-ray image and sweeps a reference line of the navigator from the upper limit line to the lower limit line, the image processor 120 displays cross-sectional images of the target tooth within an interest range set by sweeping the reference line, on the display unit 140. In one embodiment, the cross-sectional images, each taken along a direction crossing the longitudinal direction of the target tooth, are axial cross-sectional images taken at respectively different depths.

In one embodiment, when the dental practitioner designates a position corresponding to the root canal of the target tooth in each of some selected cross-sectional images, the image processor 120 calculates 3D coordinates of each of the designated positions and three-dimensionally renders a portion of the root canal of the target tooth in each of the selected cross-sectional images on the basis of the calculated three-dimensional coordinates. In this embodiment, the dental practitioner may designate a position corresponding to a relatively dark portion located at the center of the target tooth as the position corresponding to the root canal in each of the selected cross-sectional images. In one embodiment, the image processor estimates the three-dimensional coordinates of each position corresponding to the root canal of the target tooth in each of the remaining cross-sectional images that are not selected, reconstructs at least a portion of the root canal of the target tooth using the calculated three-dimensional coordinates and the estimated three-dimensional coordinates, displays a three-dimensionally rendered image of the root canal on the display unit 140. In this embodiment, the three-dimensional coordinates of each position corresponding to the root canal of the target tooth in each of the remaining cross-sectional images which are not selected are estimated by applying a 3D curve fitting algorithm on the calculated 3D coordinates of each position designated by the dental practitioner. In one embodiment, the image processor 120 calculates three-dimensional coordinates of each interpolated position between the calculated three-dimensional coordinates and the estimated three-dimensional coordinates, reconstructs at least a portion of the root canal of the target tooth using all of the coordinates, and three-dimensionally renders the reconstructed root canal.

The image processor 120 displays the root canal curvatures at multiple positions on a portion of the root canal in the three-dimensionally rendered image on the display unit 140 using visual factors. In one embodiment, the visual factors include symbols, characters, figures, and colors. The root canal curvatures at multiple positions in the longitudinal direction of the tooth are represented in the same manner or differently depending on the root canal curvatures. In one embodiment, in response to an operation in which the dental practitioner designates a position on the three-dimensionally rendered image of a portion of the root canal of the target tooth, the image processor 120 displays the root canal curvature at the designated position on the display unit 140 using a visual factor. Whenever the dental practitioner designates a position on the three-dimensionally rendered image of a portion of the root canal, the image processor 120 displays the root canal curvature at the designated position as a circle abutting the root canal on the display unit 140. When the dental practitioner designates a different position on the three-dimensionally rendered image of a portion of the root canal, since the curvature at that position may differ from the curvature on the previously designated position, the size of the circle at that position may differ from the size of the circle corresponding to the previously designated position. A circle abutting the root canal at each designated position may be arranged on a plane having a three-dimensionally minimum curvature. The size of the circle abutting the root canal at the designated position is determined on the basis of the value of the differential between the designated position and each of positions adjacent to the designated position. In one embodiment, the image processor 120 is configured to numerically display the radius of the circle. In one embodiment, the image processor 120 is configured to numerically display the distance between the top position of the root canal and the designated position. In one embodiment, the image processor 120 performs image processing operations so that the dental practitioner can see the shape and curvature of the root canal in an intended direction by rotating the three-dimensionally rendered image of the root canal using the input interface 110. For example, the image processor 120 is configured to display a circle according to the root canal curvature at each position in real time when the dental practitioner places a navigator on the three-dimensionally rendered image of the root canal using a mouse and and turns the mouse wheel.

Due to the functions provided by the image processor 120, the dental practitioner can recognize the curved direction of the root canal at the designated position by checking the direction of the circle face, and visually checks the size of the circle by looking at the numerical value of the radius of the circle. Therefore, the dental practitioner can intuitively recognize the root canal curvature at the designated position.

In addition, the dental practitioner can see how far the designated position is from the top of the root canal by looking at the numerical value of the distance. The use of the functions performed by the image processor 120 provides the effects described below. First, it is possible to prevent measurement errors that may occur when the curvature is measured on the basis of a two-dimensional image because the root canal curvature of a tooth that is a three-dimensional structure is measured on the basis of three-dimensional data. Second, it is possible to prevent errors that may occur when finding a largely curved portion of the root canal by eye. Third, it is possible to conveniently measure the root canal curvature because the curvature is automatically measured from a three-dimensionally reconstructed image. Finally, the dental practitioner can easily recognize the root canal curvature of a target tooth because the curvature is automatically visualized into a circle.

In terms of hardware, the image processor 120 is implemented with at least one of application specific integrated circuits (ASICs), digital signal processors (DSPs), digital signal processing devices (DSPDs), programmable logic devices (PLDs), field-programmable gate arrays (FPGAs), processors, controllers, micro-controllers, and microprocessors. Alternatively, the image processor 120 may be implemented with a firmware or software module executable on the above-described hardware platform. In this case, the firmware or software module may be implemented with one or more software applications written in an appropriate program language.

Figure 2:
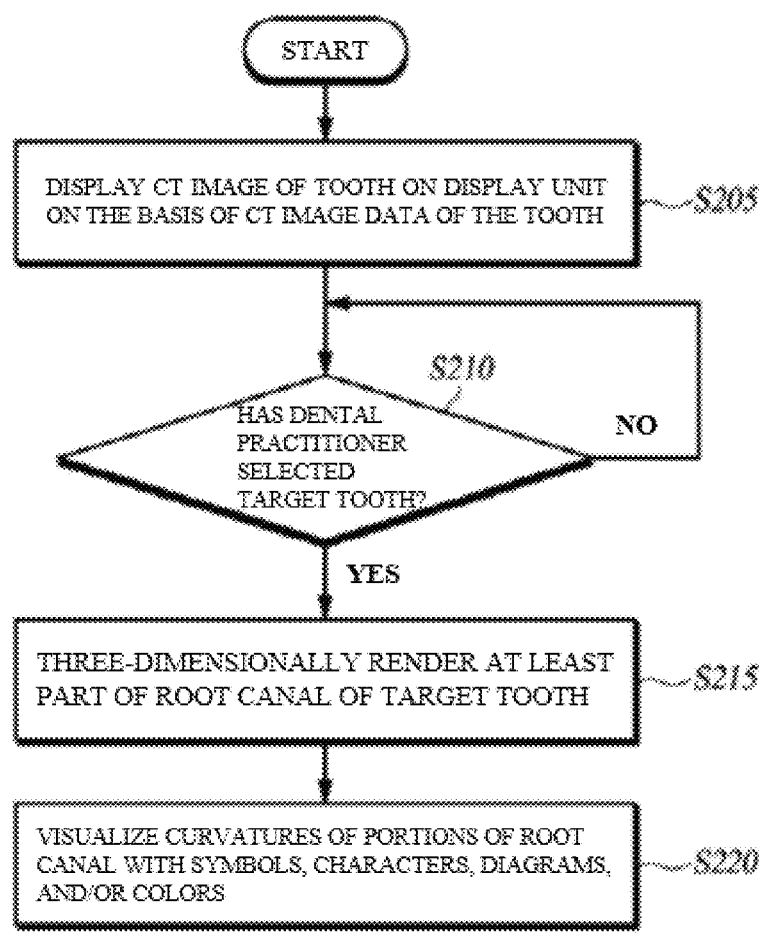
FIG. 2 is a flowchart illustrating a method of three-dimensional visualizing the root canal curvature of a tooth, according to one embodiment of the present invention.
Figure 3:
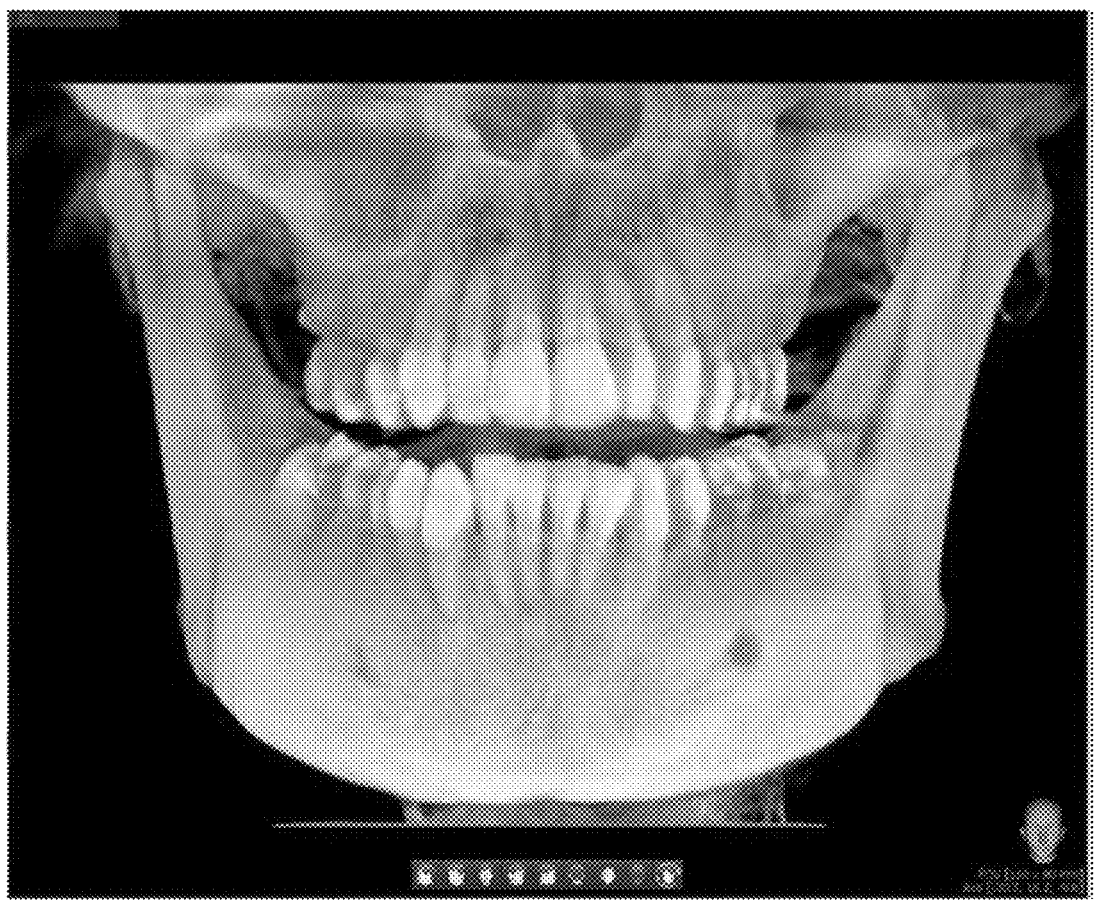
FIG. 3 is a photograph showing an example of a CT image of a tooth.
Figure 4:
FIGS. 4 and 5 are exemplary images including a panoramic X-ray image of teeth and a CT image at a plane intersecting a longitudinal direction of a target tooth.
Figure 5:

FIG. 2 is a flowchart illustrating a method of three-dimensional visualizing the root canal curvature of a tooth, according to one embodiment of the present invention. FIG. 3 is a picture showing an example of a CT image of a tooth. FIGS. 4 and 5 are exemplary images including a panoramic X-ray image of teeth and cross-sectional images at respective planes intersecting a longitudinal direction of a target tooth. FIGS. 6 through 9 are photographs that are exemplary three-dimensionally rendered images each illustrating the root canal curvature of a tooth.

As illustrated in FIG. 2, the method starts with step S205 in which a CT image of at least one tooth is displayed on a display unit 140 on the basis of CT image data of at least one tooth. FIG. 3 illustrates an exemplary CT image of a tooth. In one embodiment, a panoramic X-ray image of at least one tooth is generated from the CT image data and is displayed on the display unit 140. Exemplary panoramic X-ray images are images in upper parts of FIGS. 4 and 5, respectively. In step S210, it is checked whether a dental practitioner has selected a target tooth among one or more teeth in the CT image or the panoramic X-ray image through an input interface 110. The panorama X-ray image of the present disclosure may be for dental use so that the entire structure of the dentition can be understood at a glance based on CT image data, unlike a general two-dimensional panoramic X-ray image taken with a general dental panoramic X-ray device, and the panoramic X-ray image of the present disclosure may be linked with CT image data. When it is determined that the dental practitioner has not selected a target tooth, the operation of step S210 is performed again. On the other hand, when it is determined that the dental practitioner has selected a target tooth in step S210, at least a portion of the root canal of the target tooth is three-dimensionally rendered in step S215. In one embodiment, the selection of the target tooth among one or more teeth in the CT image or the panoramic X-ray image is performed in a manner that the dental practitioner places a navigator on the CT image or the panoramic X-ray image by using the input interface 110. In response to an operation in which the dental practitioner selects a target tooth, an operation of three-dimensionally rendering at least a portion of the root canal of the target tooth is performed automatically or manually.

In one embodiment, the automatic method is performed in a manner to calculate three-dimensional coordinates of multiple positions on the root canal of the target tooth on the basis of the CT image data by using an algorithm such as an edge detection algorithm, an image segmentation algorithm, and the like, and to three-dimensionally render at least a portion of the root canal of the target tooth on the basis of the calculated three-dimensional coordinates. The automatic method has the advantage of minimizing the intervention of a dental practitioner.

In the case of the manual method, the dental practitioner selects a target tooth, and then cross-sectional images, each being taken along a direction crossing the longitudinal direction of the target tooth, are displayed on the display unit 140 on the basis of CT image data. For example, the cross-sectional images are six images shown in the lower part of the photograph shown in FIG. 4. In one embodiment, when the dental practitioner sequentially designates multiple positions on the target tooth one after another along the longitudinal direction of the target tooth, cross-sectional images corresponding to the respective portions are displayed one after another on the display unit 140. In one embodiment, when the dental practitioner places a navigator on a target tooth on the CT image or the panoramic X-ray image and sweeps a reference line of the navigator within a range between the upper limit line to the lower limit line, cross-sectional images within the range of the target tooth are displayed on the display unit 140. In one embodiment, the cross-sectional images, each taken along a direction crossing the longitudinal direction of the target tooth, are axial cross-sectional images taken at respectively different depths.

When the cross-sectional images are displayed on the display unit 140, the dental practitioner designates positions corresponding to the root canal of the target tooth within one or more selected cross-sectional images of the displayed cross-sectional images. FIG. 5 shows an example in which the dental practitioner designates positions respectively denoted by reference numerals 1 to 6 within six cross-sectional images. However, it should be understood that it is not necessary to designate the positions corresponding to the root canal in all of the selected cross-sectional images. In addition, in the example of FIG. 5, when the dental practitioner designates a horizontal position corresponding to the root canal in a specific cross-sectional image, a vertical position (depth) corresponding to the horizontal position designated in the specific cross-sectional image is automatically marked on the corresponding panoramic X-ray image. The dental practitioner may designate a position corresponding to a relatively dark portion located at the center of the target tooth in a cross-sectional image as the horizontal position of the root canal. When the position of the root canal of the target tooth is designated in each of the selected cross-sectional images, the three-dimensional coordinates of each of the designated position is calculated, and at least a portion of the root canal of the target tooth is three-dimensionally rendered on the basis of the calculated three-dimensional coordinates. In one embodiment, at least a portion of the root canal of the target tooth may be three-dimensionally rendered on the basis of additional three-dimensional coordinates other than the calculated three-dimensional coordinates. That is, the three-dimensional coordinates of a position corresponding to the root canal of the target tooth in each of the remaining cross-sectional images are estimated, and at least a portion of the root canal of the target tooth may be reconstructed on the basis of the calculated three-dimensional coordinates and the estimated three-dimensional coordinates. In this embodiment, the three-dimensional coordinates of a position corresponding to the root canal of the target tooth in each of the remaining cross-sectional images other than the selected cross-sectional images are estimated by applying a 3D curve fitting algorithm on the calculated three-dimensional coordinates of each position designated by the dental practitioner. In another embodiment, in addition to the calculated three-dimensional coordinates of each position designated by the dental practitioner and the estimated three-dimensional coordinates, interpolated three-dimensional coordinates between the calculated three-dimensional coordinates and the estimated 3D coordinates may be further estimated. At least a portion of the root canal of the target tooth may be three-dimensionally rendered by reconstructing the portion of the root canal of the target tooth on the basis of all of those three-dimensional coordinates.

Figure 6:
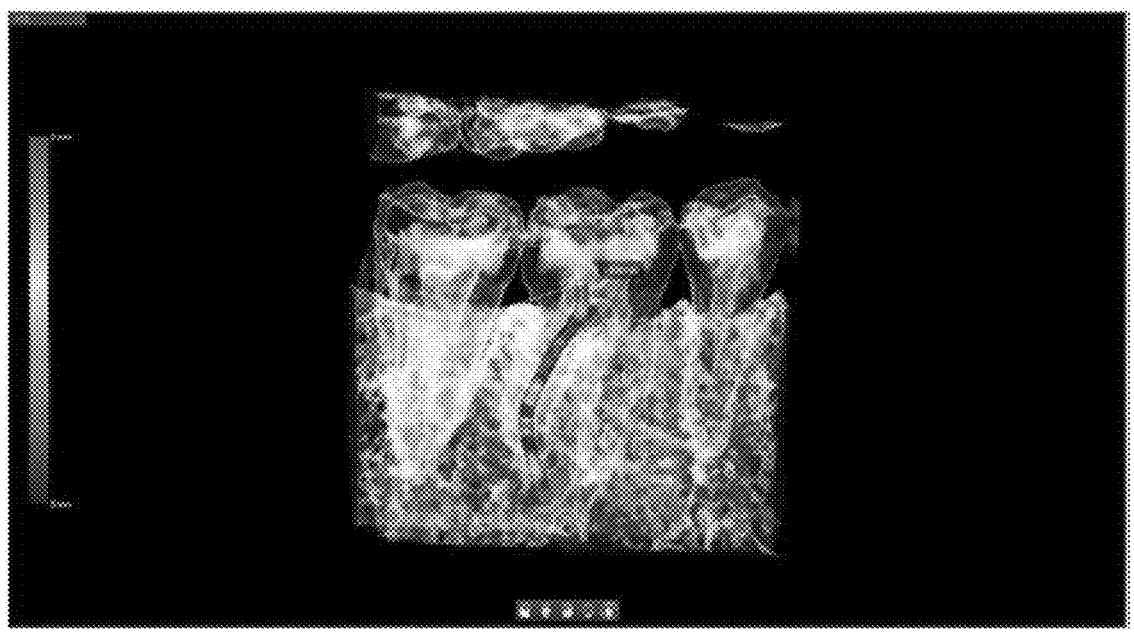
FIGS. 6 through 9 are photographs that are exemplary three-dimensionally rendered images each illustrating the root canal curvature of a tooth.
Figure 7:
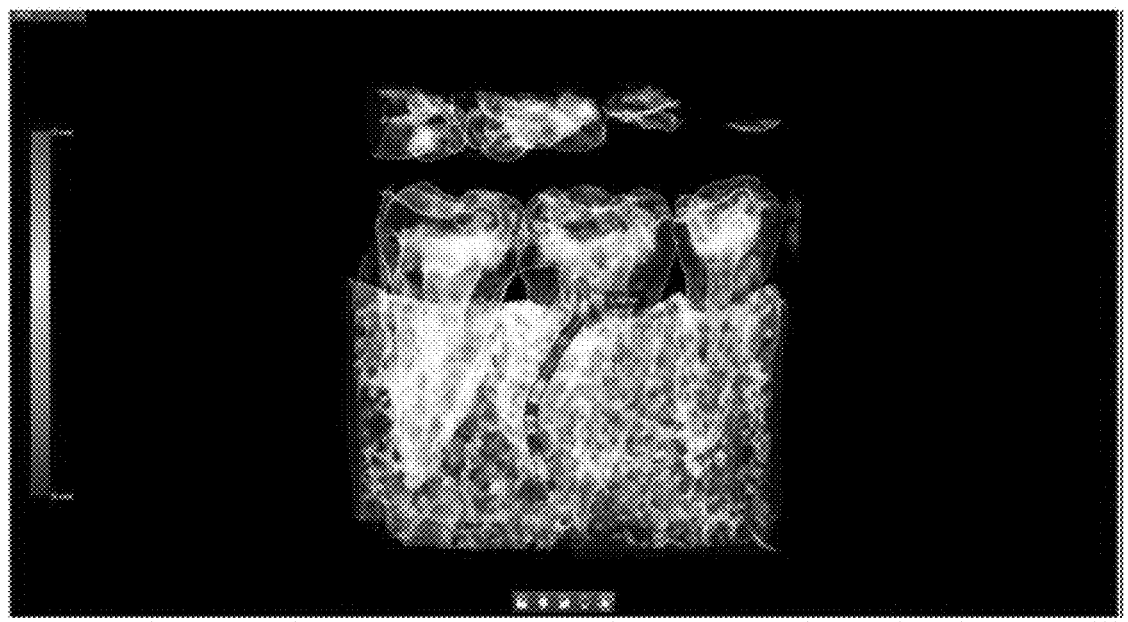
Figure 8:
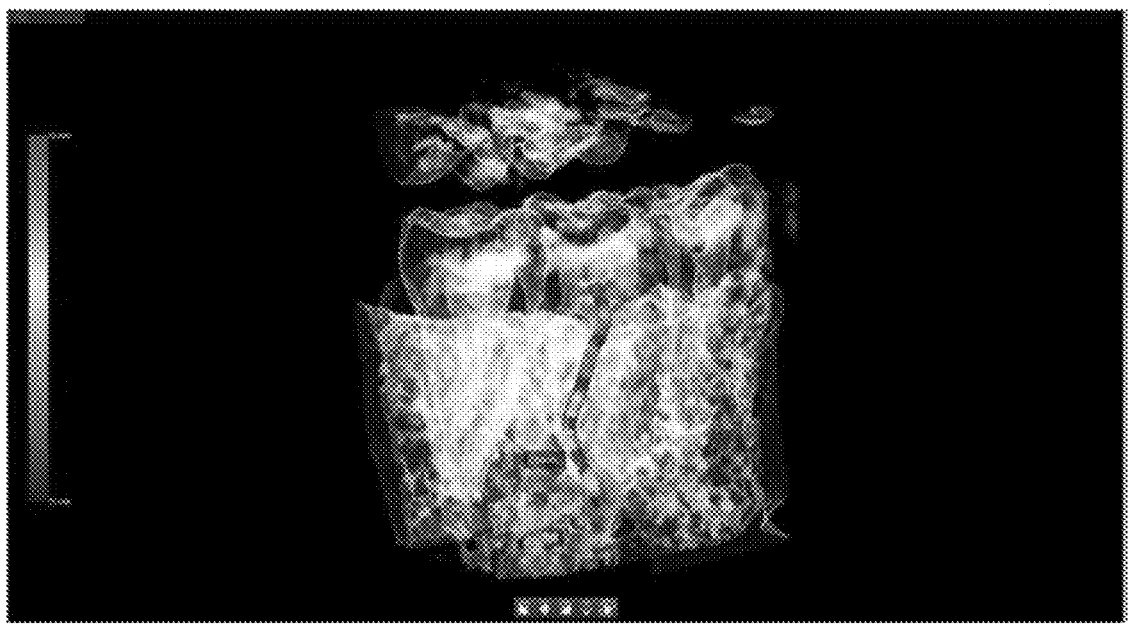
Figure 9:
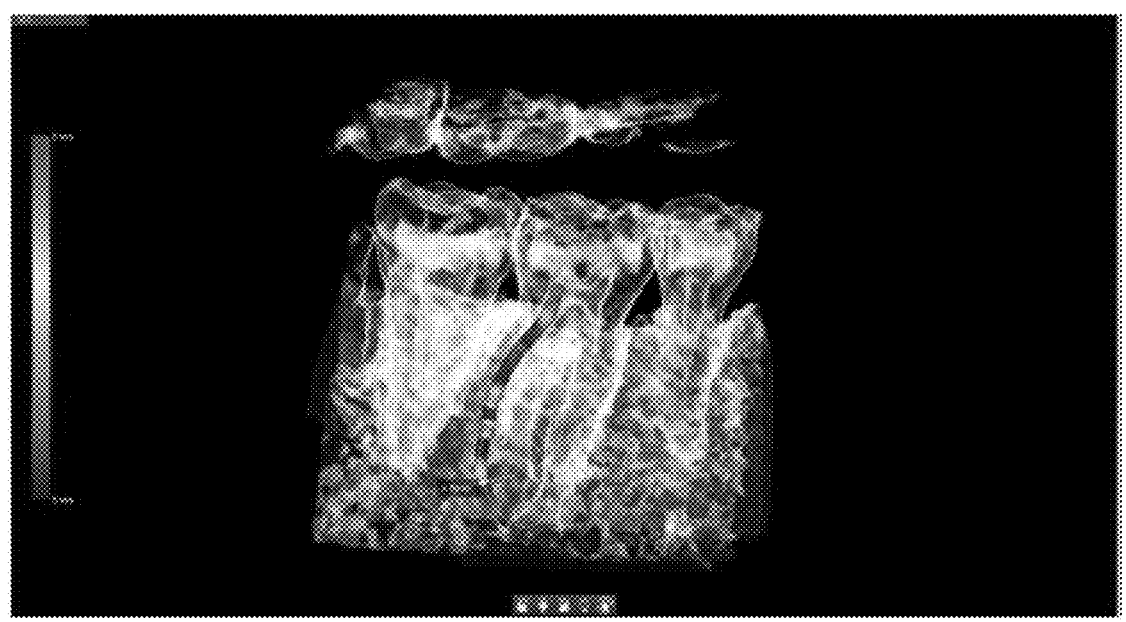

In step 220, the curvature of at least a portion of the root canal in the three-dimensionally rendered image is displayed on the display unit 140 as at least one visual factor selected from among symbols, characters, figures, and colors. FIGS. 6 through 9 are photographs that are exemplary three-dimensionally rendered images each illustrating the root canal curvature of a tooth. As illustrated in the figures, a portion of the root canal, in which the curvature is smallest, is colored blue. As the curvature increases, the color changes in order of blue, green, yellow, and red. The curvatures at respective designated positions may be the same or may differ. Thus, the curvatures at respective positions are represented visually differently or in the same manner from position to position. Referring to FIGS. 6 through 9, all of the portions colored blue represent regions with the same curvature. In one embodiment, the dental practitioner designates positions on at least a portion of the root canal on the three-dimensionally rendered image, and the curvatures at the respective designated positions are visualized in a specific form on the display unit 140. Whenever the dental practitioner designates a position on at least a portion of the root canal on the three-dimensionally rendered image, the curvature at the designated position is displayed on the display unit 140 in the form of a circle abutting the root canal. When the dental practitioner designates a different position on a portion of the root canal on the three-dimensionally rendered image, since the curvature on that position may differ from the curvature on the previously designated position, the size of the circle at that position may differ from the size of the circle corresponding to the previously designated position. In the example of FIG. 6, when a position at the top of the root canal is designated, since the root canal has a relatively small curvature at the top position, a circle having a relatively small size is displayed for the position. In the example of FIG. 7, a position slightly lower than the top position of the root canal is designated. Since the curvature at this position is slightly larger than that of the top position of the root canal, a slightly smaller circle than the previous circle shown in FIG. 6 is displayed. In the example of FIG. 8, a position that is lower than the position designated in FIG. 7 is designated, and the position is displayed in red. That is, the curvature at this position is larger than that of the previously designated position, a far smaller circle is displayed. In the example of FIG. 9, a position at the bottom of the root canal is designated, and the curvature at this position is smaller than that of the position shown in FIG. 8. Thus, a larger circle than that of FIG. 8 is displayed. Circles abutting the root canal at the respectively designated positions are arranged on a plane having a three-dimensionally minimum curvature. The size of the circle that is marked at the designated position to abut the root canal is determined on the basis of the value of the differential between the designated position and each of positions adjacent to the designated position. In one embodiment, the radius of the displayed circle is numerically displayed. In FIGS. 6 to 9, the sizes of the displayed circles are 5.00 mm, 3.41 mm, 2.54 mm and 3.76 mm, respectively. In one embodiment, the distance from the top position of the root canal to a designated position is numerically displayed. In one embodiment, when the dental practitioner rotates at least a portion of the three-dimensionally rendered image of the root canal with the use of the input interface 110, an image processing operation is performed such that the dental practitioner can see the shape and curvature of the root canal from an intended direction. For example, when the dental practitioner places a navigator at a position on the three-dimensionally rendered image of the root canal using a mouse that is an input device and turns the mouse wheel, the dental practitioner can see circles corresponding to the curvatures at respective positions in real time. Referring to FIGS. 7 to 9, it can be seen that the root canal is rotated and rendered three-dimensionally.

In the embodiments disclosed herein, the arrangement of the described or illustrated components may vary depending on environment in which the invention is implemented or depending on requirements for implementation of the invention. For example, some components may be omitted or several components may be integrated into and implemented as one module. The arrangement order and connection of some components may be changed.

Although the preferred embodiments of the present disclosure have been described for illustrative purposes, those skilled in the art will appreciate that various modifications, additions, and substitutions are possible, without departing from the scope and spirit of the present disclosure as defined in the appended claims. It is thus well known to those skilled in the art that the present invention is not limited to the embodiments disclosed in the detailed description but rather cover various modifications, additions, substitutions, and equivalents to the embodiments. Accordingly, the technical scope of the present invention should be defined by the following claims.

What is claimed is:

1. A method of three-dimensionally visualizing the curvature of the root canal of a tooth, the method comprising:
   (a) displaying a CT image of one or more teeth on the basis of CT image data of the one or more teeth;
   (b) three-dimensionally rendering at least a portion of the root canal of a target tooth when a dental practitioner selects the target tooth on the CT image; and
   (c) representing a curvature of at least a portion of the root canal that is three-dimensionally rendered in a visually identifiable manner,
   wherein in response to an operation in which the dental practitioner designates a position on at least a portion of the root canal on a three-dimensionally rendered image, the representing (step (c)) comprises visually representing a curvature at the designated position using a visual factor, and
   wherein the representing (step (c)) comprises representing a curvature at a position designated by the dental practitioner as a circle abutting the root canal and providing the dental practitioner with the radius of the circle in response to an operation in which the dental practitioner designates the position on the three-dimensionally rendered image of the root canal.

2. The method according to claim 1, further comprising: generating a panoramic X-ray image of the one or more teeth on the basis of the CT image data in between the displaying (step (a)) and the rendering (step (b)),
   wherein the rendering (step (b)) comprises three-dimensionally rendering at least a portion of the root canal of the target tooth when the dental practitioner selects the target tooth from the panoramic X-ray image.

3. The method according to claim 1, wherein the at least a portion of the root canal includes portions having different curvatures, and
   the representing (step (c)) comprises representing the curvatures of the portions in which the curvatures differ visually differently.

4. The method according to claim 1, wherein in response to an operation in which the dental practitioner sequentially designates multiple positions one after another on at least a portion of the root canal on a three-dimensionally rendered image, the representing (step (c)) comprises sequentially displaying curvatures at the respective designated positions as respective circles adjacent to the root canal one after another.

5. The method according to claim 4, wherein the circles of different sizes are three-dimensionally arranged on planes having a minimum curvature, at the designated positions, respectively.

6. The method according to claim 1, wherein the rendering (step (b)) comprises:
   displaying cross-sectional images taken along a line intersecting a longitudinal direction of the target tooth on the basis of the CT image data when the dental practitioner selects the target tooth from the CT image;
   calculating three-dimensional coordinates of each position designated by the dental practitioner in response to an operation in which the dental practitioner designates the position from one or more selected cross-sectional images of the cross-sectional images; and
   three-dimensionally rendering the root canal of the target tooth on the basis of the calculated three-dimensional coordinates.

7. The method according to claim 1, wherein the rendering (step (b)) comprises:
   displaying cross-sectional images corresponding to respectively different portions of the target tooth one after another in response to an operation in which the dental practitioner designates the portions along a longitudinal direction of the target tooth one after another;
   calculating three-dimensional coordinates of each position designated by the dental practitioner in response to an operation in which the dental practitioner designates the positions from one or more selected cross-sectional images of the cross-sectional images; and
   three-dimensionally rendering the root canal of the target tooth on the basis of the calculated three-dimensional coordinates.

8. The method according to claim 1, wherein the rendering (step (b)) comprises:
   calculating three-dimensional coordinates of the root canal of the target tooth by applying an edge detection algorithm on the CT image data; and
   three-dimensionally rendering the root canal of the target tooth on the basis of the calculated three-dimensional coordinates.

9. The method according to claim 1, wherein the representing (step (c)) comprises representing a curvature at a position designated by the dental practitioner as a circle abutting the root canal in response to an operation in which the dental practitioner designates the position on the three-dimensionally rendered image of the root canal, and
the size of the circle is determined on the basis of a differential value between the designated position and each of positions adjacent to the designated position.

10. The method according to claim 1, wherein the representing (step (c)) comprises representing a curvature at a position designated by the dental practitioner as a circle abutting the root canal and providing the dental practitioner with a distance between the uppermost position of the root canal and the designated position in response to an operation in which the dental practitioner designates the position on the three-dimensionally rendered image of the root canal.

11. The method according to claim 1, wherein the representing (step (c)) comprises displaying at least one curvature in at least a portion of the root canal on the three-dimensionally rendered image as at least one visual factor selected from among a symbol, a character, a figure, and a color.

* * * * *